United States Patent
Bruening et al.

(10) Patent No.: US 7,799,333 B2
(45) Date of Patent: Sep. 21, 2010

(54) EMULSIFIER MIXTURE CONTAINING FATTY ALCOHOLS, ETHOXYLATED FATTY ALCOHOLS AND OIL AND WAX COMPONENTS

(75) Inventors: Stefan Bruening, Duesseldorf (DE); Achim Ansmann, Erkrath (DE); Helga Gondek, Duesseldorf (DE)

(73) Assignee: Cognis IP Management GmbH, Duesseldorf (DE)

( * ) Notice: Subject to any disclaimer, the term of this patent is extended or adjusted under 35 U.S.C. 154(b) by 1253 days.

(21) Appl. No.: 10/484,925

(22) PCT Filed: Jul. 18, 2002

(86) PCT No.: PCT/EP02/08012

§ 371 (c)(1),
(2), (4) Date: Jan. 26, 2004

(87) PCT Pub. No.: WO03/011421

PCT Pub. Date: Feb. 13, 2003

(65) Prior Publication Data

US 2004/0234563 A1 Nov. 25, 2004

(30) Foreign Application Priority Data

Jul. 27, 2001 (DE) ................................. 101 36 483

(51) Int. Cl.
*A61K 8/00* (2006.01)
*A61K 8/02* (2006.01)
(52) U.S. Cl. .................................................... 424/401
(58) Field of Classification Search .................. 424/401
See application file for complete search history.

(56) References Cited

U.S. PATENT DOCUMENTS

| 4,172,887 | A | 10/1979 | Vanlerberghe et al. |
| 5,494,938 | A | 2/1996 | Kawa et al. |
| 5,714,154 | A | 2/1998 | Le Hen-Ferrenbach et al. |
| 5,718,891 | A | 2/1998 | Prat et al. |
| 5,795,978 | A | 8/1998 | Ansmann et al. |
| 5,958,431 | A | 9/1999 | Brancq et al. |
| 6,623,746 | B1 * | 9/2003 | Wadle et al. ............. 424/402 |
| 6,835,700 | B1 * | 12/2004 | Nieendick et al. ......... 510/119 |
| 2003/0053970 | A1 | 3/2003 | Bruening et al. |

FOREIGN PATENT DOCUMENTS

| DE | 195 11 668 | 10/1996 |
| DE | 198 31 705 | 3/1999 |
| DE | 19827661 A1 * | 12/1999 |
| DE | 199 43 585 | 3/2001 |
| EP | 0 771 558 | 5/1997 |
| FR | 2 252 840 | 11/1974 |
| JP | A-06-502117 | 3/1994 |
| WO | WO 92 07543 | 5/1992 |
| WO | WO 94 14877 | 7/1994 |
| WO | WO 94 21593 | 9/1994 |
| WO | WO 94 22414 | 10/1994 |
| WO | WO 97 18033 | 5/1997 |
| WO | 99/11235 | 3/1999 |
| WO | WO 99 66898 | 12/1999 |
| WO | WO 00 04230 | 1/2000 |
| WO | 00/35415 | 6/2000 |
| WO | WO 0068350 A1 * | 11/2000 |
| WO | 01/00149 | 1/2001 |
| WO | 01/52806 | 7/2001 |
| WO | WO 01 52806 | 7/2001 |

OTHER PUBLICATIONS

Flick, E. W. Emulsifying Agents: An Industrial Guide. N.J., Noyes Publications, 1990. pp. 104, 146-155.*
Full Translation of Ferrenbach (WO 99/66898).*
Cabeza et a;/, "Influencia sobre la consistencia de cremas O/W en dependencia de su elaboraciÓn γ formulación", SÖFW Journal, vol. 120, 1994, pp. 162, 164, 166, 169-172, 174-176.
P. Hameyer, "The effect of emulsifiers and emulgands on the consistency-developing structures of creamy o/w emulsions", SÖFW Journal, vol. 121, 1995, p. 216, 218-220, 222, 224, 226.
Shaikh et al., "Organic Carbonates", Chem.Rev., 1996, vol. 96, pp. 951-976.
J. Falbe, "Surfactants in Consumer Products", Springer Verlag, 1987, pp. 54-124.
Falbe et al., "Katalysatoren, Tenside und Mineralöladditive", Thieme Verlag, Stuttgart, 1978, pp. 123-217.
"Kosmetische Färbemittel", Farbstoffkommission der Deutschen Forschungsgemeinschaft, 1984, pp. 81-106.

* cited by examiner

*Primary Examiner*—Yong S Chong
*Assistant Examiner*—Jody L Karol

(57) ABSTRACT

A composition comprising: (a) from about 0.1 to 60%, by weight, of one or more fatty alcohols; (b) from about 30 to 97%, by weight, of one or more ethoxylated fatty alcohols; (c) from about 0.1 to 20%, by weight, of a component selected from the group consisting of a dialkyl ether, a dialkenyl ether, and mixtures thereof; and (d) less than 5%, by weight, of water, all weights being based on the weight of the composition, which composition is useful as an emulsifier for cosmetic and pharmaceutical compositions, particularly for forming low-viscosity oil-in-water emulsions.

13 Claims, No Drawings

EMULSIFIER MIXTURE CONTAINING FATTY ALCOHOLS, ETHOXYLATED FATTY ALCOHOLS AND OIL AND WAX COMPONENTS

BACKGROUND OF THE INVENTION

This application is a 371 of PCT/EP02/08012 filed Jul. 18, 2002.

This invention relates to a new emulsifier compound with particular contents of fatty alcohols, ethoxylated fatty alcohols and selected oil and wax components and to the use of the emulsifier compounds for the production of cosmetic and/or pharmaceutical preparations.

Consumers expect cosmetic skin- and hair-care emulsions to satisfy a range of requirements. Apart from the cleaning and skin-/hair-care effects which determine the intended application, value is placed on such diverse parameters as very high dermatological compatibility, elegant appearance, optimal sensory impression and stability in storage. Some of these features, such as dermatological compatibility for example, can largely be objectively determined by the cosmetic chemist. However, when it comes to sensory impression, evaluation by volunteers is, ultimately, always subjective.

From the emulsion technology perspective, it is particularly important to provide emulsifiers and emulsifier combinations which produce fine-droplet and storable emulsions. Accordingly, there is always interest in the development of new emulsifier combinations which enable particularly stable, fine-droplet emulsions to be formulated. Reference may be made in this connection to the articles by A. Ansmann [Seifen-Öle-Fette-Wachse, 117, 518 (1991)], C. Cabeta [SÖFW-Journal, 120, 162 (1994)], P. Hameyer [SÖFW-Journal, 121, 216 (1995)] and, in particular, A. Wadle [Parf. Kosm. 77, 250 (1996)].

Although the expert knows of measures by which, in principle, fine-droplet and storable emulsions can be obtained, known emulsions are still not entirely satisfactory due to the choice of emulsifiers used. Emulsions are normally stabilized by a combination of emulsifiers. The self-emulsifiable mixtures based on fatty alcohols known, for example, from EP 0 553 241 (SEPPIC) or WO 97/18033 (fatty alcohol/alkyl polyglycoside mixtures) are often used for this purpose. The emulsifier mixtures obtainable under the names of Cetomacrogol® Emulsifying Wax (British Pharmacopeia), Cire de Lanol® CTO (Seppic S.A.), Sinnowax® AO (Cognis France, S.A.), Promulgen® D (Amerchol) are mentioned solely as examples of the fatty alcohol/fatty alcohol ethoxylate combination. Emulsifier mixtures based on fatty alcohol/alkyl polyglucoside/partial glyceride are known from International patent application WO 92/07543.

The emulsifier mixtures commercially available at the present time are often unsuitable for the production of low-viscosity o/w emulsions for which there is presently an increasing demand on the cosmetics market. Besides poor emulsion stability, changes in viscosity often occur during storage, particularly at elevated temperatures. At the same time, viscosity is often dependent on the shear rate in the industrial production process, so that products with different viscosities are obtained from different production plants. Such variations are not acceptable in the manufacture of cosmetic products or to the consumer.

Accordingly, the problem addressed by the present invention was to provide emulsifier mixtures (compounds) for the production of cosmetic products, more particularly thinly liquid low-viscosity o/w emulsions, with which it would be possible to obtain stable emulsions whose viscosity would not be affected by the shear rate during production and would not change even during storage under temperature stress (−5 to 50° C.). In addition, the emulsifier mixtures would have good skin-care effects and improved sensory properties that would allow the production of sensorially "lights" products. Another problem addressed by the invention was to provide emulsifier mixtures that would enable the formation of microfoam on the skin—known among experts as "white residue"—to be reduced. A further problem addressed by the invention was to provide emulsifier mixtures that would enable stable emulsions with a high salt content to be produced.

DESCRIPTION OF THE INVENTION

It has been found that emulsifier mixtures with a particular content of fatty alcohols, fatty alcohol ethoxylates and special oil or wax components not only have excellent sensory and care properties, they also afford advantages from the emulsion technology perspective.

The present invention relates to emulsifier mixtures containing
  (a) 0.1 to 60% by weight of a fatty alcohol or fatty alcohol mixture,
  (b) 30 to 97% by weight of an ethoxylated fatty alcohol or mixture of ethoxylated fatty alcohols,
  (c) 0.1 to 20% by weight of a dialk(en)yl ether, a dialk(en)yl carbonate or a mixture of these components,
  (d) less than 10% by weight of water.

Components (a), (b) and (c) of the emulsifier compositions according to the invention may also add up to 100%, i.e. the emulsifier composition could consist largely of these components except for secondary products originating from the raw materials used and residual water, although such secondary products and residual water may be present. However, the emulsifier mixture according to the invention may also contain other components. The quantity of water in the emulsifier mixture is less than 10% by weight and preferably less than 5% by weight.

Highly stable emulsions, more particularly thinly liquid low-viscosity o/w emulsions, can be produced with the emulsifier mixtures according to the invention. The resulting emulsions are particularly stable in storage and do not undergo any significant changes in viscosity, even under temperature stress (storage conditions: 84 days at −5 to 50° C.). The "compounds" according to the invention allow the formulation of emulsions whose viscosity is not dependent on the shear rate during the production process. In addition, the combination according to the invention contributes towards a reduction in microfoam formation which often occurs in emulsions containing wax components. In particular, very light and stable emulsions with relatively high salt concentrations, more especially thinly liquid antiperspirant roll-on formulations containing aluminum chlorohydrates and similar salts, can be produced using the emulsifier mixture according to the invention.

A preferred embodiment of the emulsifier mixture contains a combination of (a) 2 to 60% by weight of a fatty alcohol or fatty alcohol mixture, (b) 30 to 90% by weight of an ethoxylated fatty alcohol or mixture of ethoxylated fatty alcohols and (c) 0.2 to 15% by weight of a dialk(en)yl ether, a dialk(en)yl carbonate or a mixture of these components. A particularly preferred embodiment contains a combination of (a) 10 to 55% by weight of a fatty alcohol or fatty alcohol mixture, (b) 30 to 85% by weight of an ethoxylated fatty alcohol or mixture of ethoxylated fatty alcohols and (c) 0.5 to 15% by weight of an dialk(en)yl ether, a dialk(en)yl carbonate or a mixture of these components.

The present invention also relates to the use of the emulsion concentrates according to the invention for the production of cosmetic and pharmaceutical preparations. The emulsion mixtures are preferably used for the production of o/w emulsions. In a particularly preferred embodiment, they are used for stabilizing thinly liquid o/w emulsions with viscosities of 100 to 20,000 mPa·s (Brookfield RVF, spindle 5, 10 r.p.m., 23° C.), more particularly for the production of antiperspirant roll-on formulations.

Fatty Alcohols (Emulsifier Component a)

Fatty alcohols in the context of the invention are primary aliphatic, branched or unbranched, saturated or unsaturated, optionally hydroxy-substituted alcohols with a $C_{6-54}$ hydrocarbon radical.

Typical examples are caproic alcohol, caprylic alcohol, 2-ethylhexyl alcohol, capric alcohol, lauryl alcohol, isotridecyl alcohol, myristyl alcohol, cetyl alcohol, isocetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, ricinolyl alcohol, hydroxystearyl alcohol, dihydroxystearyl alcohol, arachyl alcohol, gadoleyl alcohol, behenyl alcohol, erucyl alcohol and brassidyl alcohol and the technical mixtures thereof obtained, for example, in the high-pressure hydrogenation of technical methyl esters based on fats and oils or aldehydes from Roelen's oxo synthesis and as monomer fraction in the dimerization of unsaturated fatty alcohols. Other examples are the Guerbet alcohols based on $C_{6-18}$ fatty alcohols and technical dimer diols and trimer triols containing 18 to 36 or 18 to 54 carbon atoms which emanate from the oligomerization and subsequent hydrogenation of unsaturated fatty acids.

Emulsifier mixtures of which the fatty alcohol component (a) is selected from the group of $C_{12-24}$ fatty alcohols are preferred for the purposes of the invention. A particularly preferred embodiment is characterized by the use of technical $C_{16-18}$ fatty alcohols such as, for example, cetylstearyl alcohol, isostearyl alcohol and Guerbet alcohols of corresponding chain length. It is particularly preferred to use $C_{16}$, $C_{18}$ and $C_{16/18}$ fatty alcohols in a quantity of 0.1 to 60% by weight and more particularly 10 to 55% by weight, based on the overall composition of the emulsifier mixture.

Fatty Alcohol Ethoxylates (Component b)

Fatty alcohol ethoxylates suitable for use as component (b) are products of the addition of ethylene oxide onto primary alcohols. The ethoxylates are produced by known methods and are basically mixtures. Depending on their production, they may have a conventional broad homolog distribution or a narrow homolog distribution. The degree of ethoxylation (EO: number of ethylene oxide units added on) represents a Gauss distribution, the maximum of the Gauss curve being referred to here as the average degree of ethoxylation n.

According to the invention, a combination of addition products with a low (n=1 to 5 EO) and relatively high average degree of ethoxylation (n=6-35 EO) is preferred. The EO figures are always based on the maximum of the Gauss distribution, i.e. the average degree of ethoxylation. Component (b) of the emulsifier mixture according to the invention preferably contains a combination of (b1) a $C_{12-24}$ fatty alcohol+1 to 5 EO and (b2) a $C_{12-24}$ fatty alcohol+6 to 35 EO. A particularly preferred embodiment of the invention is characterized by the use of a three-component combination in which component (b) contains a mixture of (b1) $C_{12-24}$ fatty alcohols+1 to 5 EO, (b2) $C_{12-24}$ fatty alcohols+6 to 16 EO and (b3) $C_{12-24}$ fatty alcohols+18 to 35 EO. A combination of (b1) $C_{18}$ fatty alcohol+1 to 2 EO, (b2) $C_{16/18}$ fatty alcohol+10 to 12 EO and (b3) $C_{16/18}$ fatty alcohol+18 to 22 EO is most particularly preferred. The three-component combination is advantageous from the emulsion technology perspective, so that particularly stable emulsions are formed, and also leads to products with better sensory properties. A particularly preferred combination of component (b) is a mixture of Eumulgin® S, Eumulgin® B1 and Eumulgin® B2 which are marketed by Cognis Deutschland GmbH. Eumulgin® S is a mixture of stearyl alcohol and Steareth-2.

The production of these nonionic surfactants corresponds to the foregoing description. Typical examples are products of the addition of ethylene oxide onto caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and technical mixtures thereof. The addition products of ethylene oxide onto cetearyl alcohol, stearyl alcohol, isostearyl alcohol or behenyl alcohol are particularly preferred.

Dialk(en)yl Ethers and Dialk(en)yl Carbonates (Component C)

The purposeful choice of component (c)—even when added in a relatively small quantity—gives the emulsifier mixture better sensory properties. The resulting emulsions formulated with the mixture according to the invention are more stable and impart a lighter and less greasy feeling on the skin. Component (c) is present in a quantity of 0.1 to 20% by weight, preferably 0.2 to 15% by weight, 0.5 to 15 and more particularly 0.5 to 5% by weight, based on the overall composition of the emulsifier mixture.

The dialk(en)yl ethers may be symmetrical or nonsymmetrical, branched or unbranched, saturated or unsaturated. $C_{6-32}$ dialkylethers such as, for example, di-n-octyl ether, di-(2-ethylhexyl)-ether, lauryl methyl ether or octyl butyl ether and didodecyl ether are particularly suitable for the purposes of the invention. $C_{16-32}$ dialkylethers are most particularly preferred because they also act as consistency factors. $C_{16-24}$ dialkylethers are particularly preferred, distearyl ether and dibehenyl ether being the most suitable.

The compounds may be prepared from fatty alcohols in the presence of acidic catalysts by generally known methods, cf. for example DE 195 11 668 A1 and DE 198 31 705 A1 and DE 199 43 585. Typical examples of such ethers are products obtained by etherification of caproic alcohol, caprylic alcohol, 2-ethylhexyl alcohol, capric alcohol, lauryl alcohol, myristyl alcohol, cetyl alcohol, palmitoleyl alcohol, stearyl alcohol, isostearyl alcohol, elaidyl alcohol, petroselinyl alcohol, linolyl alcohol, linolenyl alcohol, oleyl alcohol, ricinolyl alcohol, elaeostearyl alcohol, arachidyl alcohol, gadoleyl alcohol, behenyl alcohol, erucyl alcohol and brassidyl alcohol, Guerbet alcohols and the technical mixtures thereof obtained, for example, in the high-pressure hydrogenation of technical methyl esters based on fats and oils.

The dialk(en)yl carbonates may be symmetrical or nonsymmetrical, branched or unbranched, saturated or unsaturated. Among the dialk(en)yl carbonates, linear or branched, saturated or unsaturated $C_{6-32}$ dialkyl(ene) carbonates, such as dihexyl, dioctyl, di-(2-ethylhexyl) or dioleyl carbonate for example, are preferred for the purposes of the invention. Wax-like $C_{16-32}$ dialkyl(ene) carbonates are particularly preferred because they also act as consistency factors. $C_{16-24}$ dialkyl(ene) carbonates are particularly preferred and, of these, saturated unbranched $C_{16-22}$ dialkyl carbonates are preferred, distearyl carbonate being particularly suitable.

The compounds may be prepared by transesterification of dimethyl or diethyl carbonate with the corresponding hydroxy compounds by known methods; a relevant overview can be found in Chem. Rev. 96, 951 (1996). Typical examples of dialkyl(ene) carbonates are transesterification products of dimethyl and/or diethyl carbonate with caproic alcohol, caprylic alcohol, 2-ethylhexyl alcohol, capric alcohol, lauryl alcohol, myristyl alcohol, cetyl alcohol, palmitoleyl alcohol, stearyl alcohol, isostearyl alcohol, elaidyl alcohol, petroselinyl alcohol, linolyl alcohol, linolenyl alcohol, oleyl alcohol, ricinolyl alcohol, elaeostearyl alcohol, arachidyl alcohol, gadoleyl alcohol, behenyl alcohol, erucyl alcohol and brassidyl alcohol, Guerbet alcohols and the technical mixtures thereof obtained, for example, in the high-pressure hydrogenation of technical methylesters based on fats and oils.

A preferred embodiment of the emulsifier mixture contains the following components:
 (a) 0.1-60% by weight of a $C_{12-24}$ fatty alcohol,
 (b1) 10-65% by weight of a $C_{12-24}$ fatty alcohol+1-5 EO,
 (b2) 10-30% by weight of a $C_{12-24}$ fatty alcohol+6-16 EO,
 (b3) 10-20% by weight of a $C_{12-24}$ fatty alcohol+18-35 EO and
 (c) 0.1 to 15% by weight of a $C_{6-32}$ dialk(en)yl ether, a $C_{6-32}$ dialk(en)yl carbonate or a mixture of these components.

Partial Glycerides

In another preferred embodiment, the emulsifier mixture according to the invention additionally contains a partial glyceride. Partial glycerides support the development of lamellar phases in the aqueous phase of the emulsions which leads to a further improvement in the skin-care effect on application to the skin. The partial glyceride may be present in a quantity of 0.1 to 10% by weight, preferably 0.1 to 5% by weight and more particularly 0.1 to 3% by weight, based on the overall composition of the emulsifier mixture.

Fatty acid partial glycerides are known substances which may be prepared by the relevant methods of preparative organic chemistry. They are normally mixtures of mono- and diglycerides which are obtained by transesterification of the corresponding triglycerides with glycerol or by selective esterification of fatty acids. The mixtures may still contain small quantities of triglycerides from the production process. The removal of unreacted starting materials and the enrichment of monoglycerides in the mixtures are normally achieved by molecular distillation. Typical examples are technical mono- and/or diglycerides derived from the following fatty acids: caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils and in the oxidation of aldehydes from Roelen's oxosynthesis. The use of partial glycerides based on stearic acid or tallow fatty acid is particularly preferred.

Among the fatty acids, unbranched, saturated $C_{8-24}$ fatty acids, especially $C_{12-18}$ fatty acids, are preferred for the purposes of the invention. In a preferred embodiment, the emulsifier mixture contains a $C_{12-18}$ partial glyceride. A particularly preferred embodiment of the invention is characterized by the use of partial glycerides selected from the group of glycerol monoesters or by the use of technical mixtures with a glycerol monoester content of 30 to 90% by weight. Such mixtures show the most optimal development of lamellar phases and hence the most optimal skin-care effect.

Another preferred embodiment of the emulsifier mixture contains
 (a) 0.1-60% by weight of a $C_{12-24}$ fatty alcohol,
 (b1) 10-65% by weight of a $C_{12-24}$ fatty alcohol+1-5 EO,
 (b2) 10-30% by weight of a $C_{12-24}$ fatty alcohol+6-16 EO,
 (b3) 10-20% by weight of a $C_{12-24}$ fatty alcohol+18-35 EO,
 (c) 0.1 to 15% by weight of a $C_{6-32}$ dialk(en)yl ether, a $C_{6-32}$ dialk(en)yl carbonate or a mixture of these components,
 (d) 0.1 to 10% by weight of a $C_{12-28}$ partial glyceride.

Cosmetic and Pharmaceutical Preparations

The emulsifier compound according to the invention is advantageously used for the production of cosmetic and pharmaceutical body-care and cleaning preparations such as, for example, lotions, sprayable emulsions, sun protection compositions, shampoos, shower baths, antiperspirants, etc. Accordingly, the present invention also relates to cosmetic preparations containing 2 to 20% by weight of the emulsifier concentrates. These cosmetic preparations are o/w emulsions with a water content of preferably more than 50% by weight, based on the preparation. These preparations normally contain a number of other components typically encountered in cosmetic products, such as fats, oils, ester oils, waxes, humectants and hydrotropes, other emulsifiers and co-emulsifiers, surfactants, solubilizers, inflammation inhibitors, active principles, thickeners, plant extracts, etc. and water. Some classes of the compounds in question are mentioned purely by way of example in the following.

Oil Components

Suitable oil components are, for example, Guerbet alcohols based on $C_{6-18}$ and preferably $C_{8-10}$ fatty alcohols, esters of linear $C_{6-20}$ fatty acids with linear $C_{6-20}$ fatty alcohols, esters of linear $C_{6-18}$ fatty acids with branched alcohols, more particularly 2-ethylhexanol, esters of linear and/or branched fatty acids with polyhydric alcohols (such as, for example, dimer diol or trimer triol) and/or Guerbet alcohols, triglycerides based on $C_{6-10}$ fatty acids, vegetable oils, branched primary alcohols, substituted cyclohexane, Guerbet carbonates, dialkyl(ene) ethers, dialkyl(ene) carbonates and/or aliphatic or naphthenic hydrocarbons and silicone oils, dimethicones or cyclomethicones. The quantity of oil components in the cosmetic preparations is normally between 1 and 20% by weight and preferably between 1 and 15% by weight, based on the overall composition of the preparation.

Surfactants

The emulsions obtainable with the aid of the emulsifiers according to the invention may contain additional anionic, nonionic, cationic and/or amphoteric or zwitterionic surfactants and emulsifiers as further components according to the particular application envisaged.

Typical examples of anionic surfactants, which are used above all in shower baths and shampoo formulations, are alkyl benzenesulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, acyl lactylates, acyl tartrates, acyl glutamates, acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution.

Typical examples of nonionic surfactants/emulsifiers are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers, fatty acid N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution.

Typical examples of cationic surfactants are quaternary ammonium compounds and esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines.

The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123-217.

Other Auxiliaries and Additives

The emulsions may be used as skin-care preparations such as, for example, day creams, night creams, skin-care creams, nourishing creams, body lotions, ointments and the like and may contain co-emulsifiers, cationic polymers, silicones, superfatting agents, fats, waxes, stabilizers, biogenic agents, glycerol, preservatives, dyes and perfumes as further auxiliaries and additives.

Suitable cationic polymers are, for example, cationic cellulose derivatives, cationic starch, copolymers of diallyl ammonium salts and acrylamides, quaternized vinyl pyrrolidone/vinyl imidazole polymers such as, for example, Luviquat® (BASF AG, Ludwigshagen/FRG), condensation products of polyglycols and amines, quaternized protein polypeptides such as, for example, Lauryldimonium Hydroxypropyl Hydrolyzed Collagen (Lamequat® L, Grünau GmbH), polyethyleneimine, cationic silicone polymers such as, for example, amodimethicone or Dow Corning (Dow Corning Co., USA), copolymers of adipic acid and dimethylaminohydroxypropyl diethylenetriamine (Cartaretine®, Sandoz/CH), polyaminopolyamides as described, for example, in FR-A 2252840 and crosslinked water-soluble polymers thereof, cationic chitin derivatives such as, for example, quaternized chitosan, optionally in microcrystalline distribution, cationic guar gum such as, for example, Jaguar® CBS, Jaguar®C-17, Jaguar® C-16 of Celanese/USA and quaternized ammonium salt polymers such as, for example, Mirapol® A-15, Mirapol® AD-1, Mirapol® AZ-1 of Miranol/USA.

Suitable silicone compounds are, for example, dimethyl polysiloxanes, methylphenyl polysiloxanes, cyclic silicones and amino-, fatty acid-, alcohol-, polyether-, epoxy-, fluorine- and/or alkyl-modified silicone compounds. Superfatting agents may be selected from such substances as, for example, polyethoxylated lanolin derivatives, lecithin derivatives, polyol fatty acid esters, monoglycerides and fatty acid alkanolamides, the fatty acid alkanolamides also serving as foam stabilizers. Typical examples of fats are glycerides while suitable waxes are inter alia beeswax, paraffin wax or microwaxes, optionally in combination with hydrophilic waxes, for example cetyl stearyl alcohol. Metal salts of fatty acids such as, for example, magnesium, aluminum and/or zinc stearate may be used as stabilizers. In the context of the invention, biogenic agents are, for example, plant extracts and vitamin complexes. Suitable preservatives are, for example, phenoxyethanol, formaldehyde solution, parabens, pentanediol or sorbic acid. Suitable pearlizing components are, for example, glycol distearic acid esters, such as ethylene glycol distearate, and fatty acid monoglycerol esters. The dyes used may be selected from any of the substances which are approved and suitable for cosmetic purposes, as listed for example in the publication "Kosmetische Färbemittel" of the Farbstoffkommission der Deutschen Forschungsgemeinschaft, published by Verlag Chemie, Weinheim, 1984, pages 81-106.

Antiperspirant Formulations

The emulsifier mixture according to the invention may be used with most particular preference for the formulation of deodorant and antiperspirant formulations which have improved sensory properties. More particularly, thinly liquid or so-called roll-on antiperspirant formulations are often unstable because of the high salt concentration, i.e. the emulsion breaks or changes viscosity particularly easily during storage. This results in antiperspirant products with very different viscosities according to the shear rate in the production process.

By contrast, very stable and constant product properties can be established with the emulsifier mixture according to the invention. The products show a distinct reduction in microfoam formation ("white residue"). Accordingly, a preferred embodiment of the cosmetic preparations are formulations containing antiperspirant components, more particularly roll-on formulations with a viscosity of 1,000 to 20,000 mPa·s (Brookfield RVT, spindle 5, 10 r.p.m., temperature 23° C.).

The antiperspirant components are present in the compositions according to the invention in a quantity of 0.1 to 30% by weight, preferably 5 to 25% by weight and more particularly 10 to 25% by weight (based on the quantity of active substance). Suitable antiperspirant components are, for example, aluminum chlorohydrates, aluminum/zirconium chlorhydrates and zinc salts. These antiperspirants probably act by partially blocking the sweat glands through the precipitation of proteins and/or polysaccharides. Besides the chlorohydrates, aluminum hydroxylactates and acidic aluminum/zirconium salts may also be used. For example, an aluminum chlorohydrate which corresponds to the formula [Al$_2$(OH)$_5$Cl].2.5H$_2$O and which is particularly preferred for the purposes of the invention is commercially available under the name of Locron® from Clariant GmbH. The Aluminum Zirconium Tetrachlorohydrex Glycine complexes marketed, for example, by Reheis under the name of Rezal® 36G are also preferably used in accordance with the invention. Other suitable deodorizing components are esterase inhibitors, preferably trialkyl citrates, such as trimethyl citrate, tripropyl citrate, triisopropyl citrate, tributyl citrate and, in particular, triethyl citrate (Hydagen® CAT, Cognis Deutschland GmbH). Esterase inhibitors inhibit enzyme activity and thus reduce odor formation. The free acid is probably released through the cleavage of the citric acid ester, reducing the pH value of the skin to such an extent that the enzymes are inhibited. Other esterase inhibitors are sterol sulfates or phosphates such as, for example, lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester. Antibacterial agents which influence the germ flora and destroy or inhibit the growth of perspiration-decomposing bacteria, may also be present in the emulsions. Examples of such antibacterial agents are chitosan, phenoxyethanol and chlorhexidine gluconate. 5-Chloro-2-(2,4-dichlorophenoxy)-phenol, which is marketed under the name of Irgasan® by Ciba-Geigy of Basel, Switzerland, has also proved to be particularly effective. However, the emulsifier combination may also be used with advantage for the formulation of antiperspirant creams. Accordingly, the present invention also relates to antiperspirant creams with a viscosity of 20 to 800 Pa·s (Brookfield RVT, spindle 5, 10 r.p.m., temperature 23° C. for viscosities of 20 to 40 Pa·s and Brookfield RVT, spindle TE, 4 r.p.m., temperature 23° C. for viscosities of 40 to 800 Pa·s).

Sun Protection Formulations

Sun protection formulations are also particularly easy to formulate with the emulsifier mixture according to the invention. The UV protection factors are very easy to incorporate; the end formulations show long-term stability, even when stored under temperature stress. Accordingly, the present invention also relates to cosmetic preparations containing UV protection factors.

The UV protection factors are present in the compositions according to the invention in a total quantity of 1 to 30% by weight, preferably 5 to 25% by weight and more particularly 5 to 15% by weight (based on the quantity of active substance).

UV protection factors in the context of the invention are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

- 3-benzylidene camphor or 3-benzylidene norcamphor and derivatives thereof, for example 3-(4-methylbenzylideneycamphor;
- 4-aminobenzoic acid derivatives, preferably 4-(dimethylamino)-benzoic acid-2-ethylhexyl ester, 4-(dimethylamino)benzoic acid-2-octyl ester and 4-(dimethylaminoybenzoic acid amyl ester;
- esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);
- esters of salicylic acid, preferably salicylic acid-2-ethylhexyl ester, salicylic acid-4-isopropylbenzyl ester, salicylic acid homomenthyl ester;
- derivatives of benzophenone, preferably 2-hydroxy-4-methoxybenzophenone, 2-hydroxy-4-methoxy-4'-methylbenzophenone, 2,2'-dihydroxy-4-methoxybenzophenone;
- esters of benzalmalonic acid, preferably 4-methoxybenzalmalonic acid di-2-ethylhexyl ester;
- triazine derivatives such as, for example, 2,4,6-trianilino-(p-carbo-2'-ethyl-1'-hexyloxy)-1,3,5-triazine and Octyl Triazone;
- propane-1,3-diones such as, for example, 1-(4-tert.butylphenyl)-3-(4'-methoxyphenyl)propane-1,3-dione;
- ketotricyclo(5.2.1.0)decane derivatives.

Suitable water-soluble substances are

- 2-phenylbenzimidazole-5-sulfonic acid and alkali metal, alkaline earth metal, ammonium, alkylammonium, alkanolammonium and glucammonium salts thereof;
- sulfonic acid derivatives of benzophenones, preferably 2-hydroxy-4-methoxybenzophenone-5-sulfonic acid and salts thereof;
- sulfonic acid derivatives of 3-benzylidene camphor such as, for example, 4-(2-oxo-3-bornylidenemethyl)benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol 1789) or 1-phenyl-3-(4'-isopropylphenyl)-propane-1,3-dione. The UV-A and UV-B filters may of course also be used in the form of mixtures. Besides the soluble substances mentioned, insoluble light-blocking pigments, i.e. finely dispersed metal oxides or salts, may also be used for this purpose. Examples of suitable metal oxides are, in particular, zinc oxide and titanium dioxide and also oxides of iron, zirconium oxide, silicon, manganese, aluminum and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilized or hydrophobicized. Typical examples are coated titanium dioxides, for example Titandioxid T 805 (Degussa) and Eusolex® T2000 (Merck). Suitable hydrophobic coating materials are, above all, silicones and, among these, especially trialkoxyoctylsilanes or simethicones. So-called micro- or nanopigments, for example micronized zinc oxide, are preferably used in sun protection products.

Besides the two groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and heptathionine sulfoximine) in very small compatible dosages (for example pmole to μmole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, zinc and derivatives thereof (for example $ZnO$, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

EXAMPLES

Table 1 contains five formulations (Compounds A-E) for the emulsifier mixture according to the invention (quantities in % by weight, based on the overall composition of the emulsifier compounds).

TABLE 1

Compounds A–E according to the invention:

| | Compound | | | | |
|---|---|---|---|---|---|
| | A (w/w %) | B (w/w %) | C (w/w %) | D (w/w %) | E (w/w %) |
| EUMULGIN ® S2 | 55 | 56 | 19 | 55 | 55.5 |
| EUMULGIN ® B1 | — | 25 | 25 | 25 | 25 |
| EUMULGIN ® B2 | 42 | 17 | 17 | 17 | 17 |
| Stearyl alcohol | 1 | 1 | 37 | 1 | 1 |
| Dioctadecyl ether | 2 | 1 | 2 | — | 0.5 |
| Dioctadecyl carbonate | — | — | — | 2 | 0.5 |
| $C_{16}/C_{18}$ Fatty acid mono-/diglyceride (CUTINA ® MD) | — | — | — | — | 0.5 |

EUMULGIN ® S2: mixture of 62.5% by weight Steareth-2 and 37.5% by weight stearyl alcohol
EUMULGIN ® B1: Ceteareth-12
EUMULGIN ® B2: Ceteareth-20

TABLE 2

Antiperspirant formulations
The quantities in the Tables represent % by weight of the commercially available substances or % by weight of the emulsifier mixtures (according to Table 1), based on the formulation as a whole.
C1 and C2 are comparison formulations which are commercially available. Formulations 1 to 3 correspond to the invention.

| | Composition (% by weight) | | | | |
|---|---|---|---|---|---|
| | C1 | C2 | 1 | 2 | 3 |
| Compound A | | | 6.0 | | |
| Compound B | | | | 6.0 | |
| Compound C | | | | | 6.0 |
| Compound D | | | | | |
| BRIJ ® 72 (Steareth-2) | 2.2 | 3.0 | | | |
| BRIJ ® 76 (Steareth-21) | 1.0 | 1.5 | | | |
| ARLAMOL ® E (PPG-15 Stearyl Ether) | 4.0 | | 4.0 | | 4.0 |
| FINSOLV ® TN (C12/15 Alkylbenzoate) | | 6.0 | | 6.0 | |
| LOCRON ® L (Aluminum Chlorohydrate (solution)) | 16 | 20 | 16 | 20 | 16 |
| Water, preservative | to 100 | to 100 | to 100 | to 100 | to 100 |
| Stability (−5, 20, 40, 45, 50° C.) | − | − | + | + | + |
| Viscostability 23° C. | 0 | 0 | 0/+ | + | + |
| Dependence of viscosity on shearing | 0 | 0 | + | + | + |
| White residue (forearm) | − | − | + | + | + |
| Care | − | − | + | + | + |
| Sensory evaluation | − | − | + | + | + |

Evaluation scale:
− = negatively evaluated
0 = moderate
+ = positively evaluated

TABLE 3

Antiperspirant formulations (according to the invention)
The quantities in the Tables represent % by weight of the
commercially available substances or % by weight of the emulsifier
mixtures (according to Table 1), based on the formulation as a whole.

| | Composition (% by weight) | | | | |
|---|---|---|---|---|---|
| | 4 | 5 | 6 | 7 | 8 |
| Compound A | | | | | |
| Compound B | | 5 | 7 | | |
| Compound C | | | | 7 | |
| Compound D | | | | | 6 |
| Compound E | 6.0 | | | | |
| ARLAMOL ® E (PPG-15 Stearyl Ether) | | 3.0 | | 1.0 | |
| FINSOLV ® TN (C12/15 Alkylbenzoate) | 6.0 | | | | |
| DOW CORNING ® 245 fluid (Cyclopentasiloxane) | | | 3.0 | 1.0 | |
| CETIOL ® OE (Dicaprylyl Ether) | | 3.0 | | 1.0 | |
| CETIOL ® CC (Dicaprylyl Carbonate) | | | 3.0 | 1.0 | 3.0 |
| EUTANOL ® G | | | | | 2.0 |
| CETIOL ® S (Diethylhexylcyclohexane) | | | 1.0 | | |
| Paraffinum Liquidum (Mineral Oil) | | | | 1.0 | |
| FITODERM ® (Squalane) | | 1.0 | | 1.0 | |
| DOW CORNING ® 200 Fluid (Dimethicone) | | | 1.0 | | |
| Vaseline | | | | 1.0 | |
| LOCRON ® L (Aluminum Chlorohydrate; solution) | 20 | 25 | | | |
| REZAL ® 36 G (Aluminum Zirconium Tetrachlorohydrex Glycine; solution) | | | 25 | | 25 |
| REZAL ® 67 (Aluminum Zirconium Pentachlorohydrate; solution) | | | | 25 | |
| Water, preservative | to 100 | to 100 | to 100 | to 100 | to 100 |
| Stability (−5, 20, 40, 45, 50° C.) | + | + | + | + | + |
| Viscostability 23° C. | + | + | + | + | + |
| Dependence of viscosity on shearing | + | + | + | + | + |
| White residue (forearm) | + | + | + | + | + |
| Care | + | + | + | + | + |
| Sensory evaluation | + | + | + | + | + |

Evaluation scale:
− = negatively evaluated
0 = moderate
+ = positively evaluated

TABLE 4

Other formulations according to the invention:
9–12 antiperspirant formulations, 13–15 sun protection formulations, 9–12
face/body care formulations
The quantities in the Tables represent % by weight of the
commercially available substances or % by weight of the emulsifier
mixtures (according to Table 1), based on the formulation as a whole.

| | 9 | 10 | 11 | 12 | 13 | 14 | 15 |
|---|---|---|---|---|---|---|---|
| Compound A | | | 6.8 | | | | |
| Compound B | | 6.5 | | 15.0 | | 7.0 | |
| Compound C | | | | | | | 7.0 |
| Compound D | 5.5 | | | | | | |
| Compound E | | | | | 6.0 | | |
| ARLAMOL ® E (PPG-15 Stearyl Ether) | 1.0 | | | | | | |
| FINSOLV ® TN (C12/15 Alkylbenzoate) | | | 1.0 | | 3.0 | | |
| DOW CORNING ® DC 245 fluid (Cyclomethicone) | 1.0 | 3.0 | 1.0 | 3.0 | 4.0 | 1.0 | |
| CETIOL ® OE (Dicaprylyl Ether) | | | 1.0 | | | 3.0 | |
| CETIOL ® CC (Dicaprylyl Carbonate) | | 3.0 | 1.0 | 3.0 | | | 2.0 |
| CETIOL ® S (Diethylhexylcyclohexane) | 3.0 | 1.0 | | 1.0 | | | |
| MYRITOL ® 331 (Cocoglycerides) | | | | | 4.0 | | 6.0 |
| Paraffinum Liquidum (Mineral Oil) | | | 1.0 | | | | |
| FITODERM ® (Squalane) | | | 1.0 | | | | |
| DOW CORNING ® 200 Fluid (Dimethicone) | | 2.0 | | 2.0 | | | |
| Vaseline | 1.0 | | | | | | |
| LOCRON ® L (Aluminum Chlorohydrate; solution) | | 25 | | 25 | | | |
| REZAL ® 36 G (Aluminum Zirconium Tetrachlorohydrex Glycine; solution) | 25 | | | | | | |
| REZAL ® 67 (Aluminum Zirconium Pentachlorohydrate; solution) | | | 25 | | | | |
| Sodium phenyl benzimidazole sulfonate | | | | | 2.0 | 2.2 | |
| NEO HELIOPAN ®, Type 303 (Octocrylene) | | | | | 3.0 | | 4.0 |
| NEO HELIOPAN ®, Type MBC (4-Methylbenzylidene Camphor) | | | | | 2.0 | 3.0 | |

TABLE 4-continued

Other formulations according to the invention:
9–12 antiperspirant formulations, 13–15 sun protection formulations, 9–12 face/body care formulations
The quantities in the Tables represent % by weight of the commercially available substances or % by weight of the emulsifier mixtures (according to Table 1), based on the formulation as a whole.

|  | 9 | 10 | 11 | 12 | 13 | 14 | 15 |
|---|---|---|---|---|---|---|---|
| NEO HELIOPAN ®, Type OS (Octyl Salicylate) |  |  |  |  |  |  | 7.0 |
| NEO HELIOPAN ®, Type E 1000 (Isoamyl p-Methoxycinnamate) |  |  |  |  |  | 6.0 |  |
| EUSOLEX ® 2292 (Octyl Methoxycinnamate) |  |  |  |  | 0.5 |  |  |
| Uvinul ® T-150 (Octyl Triazone) |  |  |  |  | 2.0 |  | 2.3 |
| EUSOLEX ® 9020 (Butyl Methoxydibenzoylmethane) |  |  |  |  |  | 1.0 | 2.0 |
| Zinc Oxide (micronized and/or surface-treated) |  |  |  |  | 10 |  | 6.0 |
| Titanium Dioxide (micronized and/or surface-treated) |  |  |  |  |  | 10 |  |
| VEEGUM ® Ultra (Magnesium Aluminum Silicates) |  |  |  |  |  | 1.0 | 3.0 |
| KELTROL ® T (Xanthan Gum) |  |  |  |  |  | 5.0 |  |
| CARBOPOL ® 980 (Carbomer) |  |  |  |  |  |  |  |
| Panthenol |  |  |  |  |  |  | 1.0 |
| Bisabolol |  |  |  |  |  |  | 0.2 |
| COVITOL ® 1100 (Tocopherol/Tocopheryl Acetate) |  |  |  |  |  | 0.5 | 1.0 |
| Glycerin |  |  |  |  | 3.0 | 2.0 |  |
| Water, preservative | ad 100 | ad 100 | ad 100 | ad 100 | ad 100 | ad 100 | ad 100 |

TABLE 5

Other formulations according to the invention:
16 sun protection formulation, 17–21 face/body-care formulations
The quantities in the Tables represent % by weight of the commercially available substances or % by weight of the emulsifier mixtures (according to Table 1), based on the formulation as a whole.

|  | 16 | 17 | 18 | 19 | 20 | 21 |
|---|---|---|---|---|---|---|
| Compound A |  |  |  |  | 6 |  |
| Compound B |  |  |  | 5.5 |  |  |
| Compound C |  | 5.5 |  |  |  | 18.0 |
| Compound D | 5.5 |  | 7.5 |  |  |  |
| DOW CORNING ® 245 fluid (Cyclomethicone DC 245) |  | 2.0 |  |  | 1.0 |  |
| CETIOL ® OE (Dicaprylyl Ether) | 3.0 |  | 1.0 | 2.0 |  | 1.0 |
| CETIOL ® CC (Dicaprylyl Carbonate) |  |  | 1.0 |  |  | 1.0 |
| CETIOL ® S (Diethylhexylcyclohexane) | 2.0 |  |  |  |  |  |
| MYRITOL ® 331 (Cocoglycerides) | 1.0 | 3.0 | 2.0 |  |  | 2.0 |
| EUTANOL ® G16S (Hexyldecylstearate) | 2.0 |  |  |  | 1.0 |  |
| CEGESOFT ® SH (Shorea Stenoptera) |  |  |  | 1.0 |  |  |
| CETIOL ® SB 45 (Butyrospermum Parkii) |  |  |  | 1.0 | 1.0 |  |
| CEGESOFT ® GPO (Golden Palm Oil) |  |  |  | 1.0 |  |  |
| Vaseline |  | 1.0 |  |  | 1.5 |  |
| Natriumphenylbenzimidazolsulfonat | 2.0 |  |  |  |  |  |
| NEO HELIOPAN ®, Type BB (Benzophenone-3) | 2.0 |  |  |  |  |  |
| NEO HELIOPAN ®, Type MBC (4-Methylbenzylidene Camphor) | 1.0 |  |  |  |  |  |
| NEO HELIOPAN ®, Type E 1000 (Isoamyl p-Methoxycinnamate) | 6.0 |  |  |  |  |  |
| Zinc Oxide (micronized and/or surface-treated) | 4.0 |  |  |  |  |  |
| Titanium Dioxide (micronized and/or surface-treated) | 4.0 |  |  |  |  |  |
| CARBOPOL ® 980 (Carbomer) | 2.0 |  |  |  |  |  |
| Panthenol |  |  |  |  | 1.0 |  |
| Bisabolol |  |  |  | 1.0 |  |  |
| Butylene Glycol |  | 1.0 | 0.5 |  |  | 0.5 |
| Glycerin | 1.0 |  |  |  |  |  |
| 4 Na EDTA |  | 0.1 | 0.1 |  |  | 0.1 |
| MELHYDRAN ® (Honey extract) |  | 1.0 | 0.5 |  |  | 0.5 |
| INDINYL ® CA (Water (and) Cassia angustifolia seed polysaccharide) |  | 1.5 | 0.5 |  |  | 0.5 |
| IRVINOL ® (Octyldodecanol (and) Irvingia gabonensis kernel butter (and) Hydrogenated cocoglycerides) |  | 1.0 |  |  |  |  |
| Hibiscus esculentus extract (Hydrolyzed hibiscus esculentus extract (and) Dextrin) |  |  |  | 2.0 |  |  |
| LACTOLAN ® (Hydrolyzed milk protein) |  |  | 1.0 |  | 1.0 |  |
| DERMOSACCHARID ® GY (Water (and) Glycerin (and) Glyco-gen) |  |  |  |  | 1.0 |  |
| PHYTALBUMIN ® HGP (Glycine soja (soybean) protein) |  | 0.5 |  |  |  |  |
| PHYTALBUMIN ® HP (Aqua (and) Hibiscus esculentus) |  | 0.5 |  |  |  |  |
| Water, preservative | ad 100 | ad 100 | ad 100 | ad 100 | ad 100 | ad 100 |

APPENDIX

1. ARLAMOL® E
INCI: PPG 15 Stearyl Ether
Manufacturer: Uniqema (Brenntag)
2. BRIJ® 72
INCI: Steareth 2
Manufacturer: Uniqema (Brenntag)
3. BRIJ® 76
INCI: Steareth 10
Manufacturer: Uniqema (ICI Surfactants)
4. CEGESOFT® GPO
INCI: Palm (Elaeis Guineensis) Oil
Manufacturer: Cognis Deutschland GmbH
5. CETIOL® CC
Synonym: Dioctylcarbonat
Manufacturer: Cognis Deutschland GmbH (Henkel)
6. CETIOL® OE
INCI: Dicaprylyl Ether
Manufacturer: Cognis Deutschland GmbH (Henkel)
7. CETIOL® S
INCI: Dioctylcyclohexane (alt), Diethylhexylcyclohexane
Manufacturer: Cognis Deutschland GmbH (Henkel)
8. CETIOL® SB 45
INCI: Shea Butter, Butyrospermum Parkii (Linne)
Manufacturer: Cognis Deutschland GmbH
9. COVITOL® 1100
INCI: Tocopheryl Acetate
Manufacturer: Cognis Corporation
10. CUTINA® MD
INCI: Glyceryl Stearate
Manufacturer: Cognis Deutschland GmbH
11. DERMOSACCHARID® GY
INCI: Aqua (Water), Glycerin, Glycogen
Manufacturer: Laboratoires Serobiologiques (Cognis)
12. DOW CORNING® 200 Fluid, 100 cS
INCI: Dimethicone
Manufacturer: Dow Corning
13. DOW CORNING® 245 Fluid
INCI: Cyclopentasiloxane
Manufacturer: Dow Corning
14. EUMULGIN® S2
INCI: Steareth-2
Manufacturer: Cognis Deutschland GmbH
15. EUMULGIN® B1
INCI: Ceteareth-12
Manufacturer: Cognis Deutschland GmbH
16. EUMULGIN® B2
INCI: Ceteareth-20
Manufacturer: Cognis Deutschland GmbH
17. EUSOLEX® 9020
INCI: Butyl Methoxydibenzoylmethane
Manufacturer: Merck
18. EUTANOL® G16S
INCI: Hexyldecyl Stearate
Manufacturer: Cognis Deutschland GmbH (Henkel)
19. FINSOLV® TN
INCI: $C_{12}$-$C_{15}$ Alkyl Benzoate
Manufacturer: Finetex (Nordmann, Rassmann)
20. FITODERM®
INCI: Squalane
Manufacturer: Hispano-Quimica-S.A., Nordmann-Rassmann
21. INDINYL® CA
INCI: Water (and) Cassia angustifolia sed polysaccharide
Manufacturer: Laboratoire Serobiologique
22. LACTOLAN® LS 5879
INCI: Hydrolyzed milk protein
Manufacturer: Laboratoire Serobiologique
23. LOCRON® L
INCI: Aluminum Chlorohydrate (Lösung: 50 Gew.-% in Wasser)
Manufacturer: Clariant
24. MELHYDRAN®
INCI: Honey Extract
Manufacturer: Laboratoires Serobiologiques (Cognis)
25. MYRITOL® 331
INCI: Cocoglycerides
Manufacturer: Cognis Deutschland GmbH (Henkel)
26. NEO HELIOPAN® 303
INCI: Octocrylene
Manufacturer: Haarmann & Reimer
27. NEO HELIOPAN® BB
INCI: Benzophenone 3
Manufacturer: Haarmann & Reimer
28. NEO HELIOPAN® MBC
INCI: 4-Methylbenzylidene Camphor
Manufacturer: Haarmann & Reimer
29. NEO HELIOPAN® OS
INCI: Ethylhexyl Salicylate
Manufacturer: Haarmann & Reimer
30. PHYTALBUMIN® HGP
INCI: Glycine Soja (Soybean) Protein
Manufacturer: Laboratoire Serobiologique
31. REZAL® 36GC
INCI: Aluminum-Zirconium Tetrachlorohydrex Gly (Lösung)
Manufacturer: Reheis
32. REZAL® 67
INCI: Aluminum Zirconium Pentachlorohydrat
Manufacturer: Reheis
33. URVINOL® T 150
INCI: Octyl Triazone
Manufacturer: BASF

The invention claimed is:

1. An emulsifier consisting of:
   (a) from about 0.1 to 60%, by weight, of at least one fatty alcohol;
   (b) from about 30 to 97%, by weight, of at least one ethoxylated fatty alcohol;
   (c) from about 0.1 to 20%, by weight, of a component selected from the group consisting of dialkyl ethers, dialkenyl ethers, dialkyl carbonates, dialkenyl carbonates and mixtures thereof; and
   (d) less than 10%, by weight, of water,
   all weights being based on the weight of the composition.

2. The emulsifier of claim 1, wherein (a) is selected from the group consisting of $C_{12-24}$-fatty alcohols.

3. The emulsifier of claim 1, wherein (b) is a mixture of at least one ethoxylated $C_{12-24}$-fatty alcohol having from 1 to 5 moles of ethylene oxide and at least one ethoxylated $C_{12-24}$-fatty alcohol having from 6 to 35 moles of ethylene oxide.

4. The emulsifier of claim 1, wherein (b) is a mixture of at least one ethoxylated $C_{12-24}$-fatty alcohol having from 1 to 5 moles of ethylene oxide and at least one ethoxylated $C_{12-24}$-fatty alcohol having from 6 to 16 moles of ethylene oxide, and at least one ethoxylated $C_{12-24}$-fatty alcohol having from 18 to 35 moles of ethylene oxide.

5. The emulsifier of claim 1, wherein (c) is selected from the group consisting of $C_{6-32}$-dialkyl ethers, $C_{6-32}$-dialkenyl ethers, and mixtures thereof.

6. An emulsifier consisting of:
(a) from about 0.1 to 60%, by weight, of at least one $C_{12-24}$-fatty alcohol;
(b) from about 10 to 65%, by weight, of at least one ethoxylated $C_{12-24}$-fatty alcohol having from 1 to 5 moles of ethylene oxide;
(c) from about 10 to 30%, by weight, of at least one ethoxylated $C_{12-24}$-fatty alcohol having from 6 to 16 moles of ethylene oxide;
(d) from about 10 to 20%, by weight, of at least one ethoxylated $C_{12-24}$-fatty alcohol having from 18 to 35 moles of ethylene oxide;
(e) from about 0.1 to 15%, by weight, of a component selected from the group consisting of dialkyl ethers, dialkenyl ethers, dialkyl carbonates, dialkenyl carbonates and mixtures thereof; and
(f) less than 10%, by weight, of water,
all weights being based on the weight of the composition.

7. An emulsifier consisting of:
(a) from about 0.1 to 60%, by weight, of at least one $C_{12-24}$-fatty alcohol;
(b) from about 10 to 65%, by weight, of at least one ethoxylated $C_{12-24}$-fatty alcohol having from 1 to 5 moles of ethylene oxide;
(c) from about 10 to 30%, by weight, of at least one ethoxylated $C_{12-24}$-fatty alcohol having from 6 to 16 moles of ethylene oxide;
(d) from about 10 to 20%, by weight, of at least one ethoxylated $C_{12-24}$-fatty alcohol having from 18 to 35 moles of ethylene oxide;
(e) from about 0.1 to 15%, by weight, of a component selected from the group consisting of dialkyl ethers, dialkenyl ethers, dialkyl carbonates, dialkenyl carbonates and mixtures thereof;
(f) from about 0.1 to 10%, by weight, of at least one $C_{12-18}$-partial glyceride; and
(g) less than 10%, by weight, of water,
all weights being based on the weight of the composition.

8. A process for the preparation of a cosmetic composition comprising adding the emulsifier of claim 1 to a cosmetic composition or cosmetic composition base.

9. The process of claim 8 wherein the sole emulsifier component of said cosmetic composition is said emulsifier of claim 1.

10. An emulsifier consisting of:
(a) from about 0.1 to 60%, by weight, of at least one fatty alcohol;
(b) from about 30 to 97%, by weight, of at least one ethoxylated fatty alcohol;
(c) from about 0.1 to 20%, by weight, of a component selected from the group consisting of dialkyl ethers, dialkenyl ethers, dialkyl carbonates, dialkenyl carbonates and mixtures thereof;
(d) less than 10%, by weight, of water, and
(e) from about 0.1 to 10%, by weight, of at least one partial glyceride;
all weights being based on the weight of the composition.

11. The emulsifier of claim 10 wherein said at least one partial glyceride is selected from the group consisting of $C_{12-18}$ partial glycerides.

12. A process for the preparation of a cosmetic composition comprising adding the emulsifier of claim 10 to a cosmetic composition or cosmetic composition base.

13. The process of claim 12 wherein the sole emulsifier component of said cosmetic composition is said emulsifier of claim 10.

* * * * *